United States Patent [19]

Tsujii et al.

[11] Patent Number: 4,803,711
[45] Date of Patent: Feb. 7, 1989

[54] X-RAY INSPECTION APPARATUS

[75] Inventors: Osamu Tsujii, Fuchu; Masashi Fujii, Hachioji, both of Japan

[73] Assignee: Kabushiki Kaisha Toshiba, Kawasaki, Japan

[21] Appl. No.: 204,922

[22] Filed: Jun. 9, 1988

Related U.S. Application Data

[63] Continuation of Ser. No. 911,100, Sep. 24, 1986, abandoned.

[30] Foreign Application Priority Data

Sep. 26, 1985 [JP] Japan ................................ 60-0211034
Sep. 30, 1985 [JP] Japan ................................ 60-216520

[51] Int. Cl.$^4$ ...................... G01N 23/02; G06F 15/42
[52] U.S. Cl. ........................................ 378/4; 378/901; 364/413.16
[58] Field of Search ...................... 378/4, 6, 7, 16, 207, 378/901, 113; 364/414, 521

[56] References Cited

U.S. PATENT DOCUMENTS

| | | | |
|---|---|---|---|
| 3,940,625 | 2/1976 | Hounsfield | 378/5 |
| 4,029,963 | 6/1977 | Alvarez et al. | |
| 4,066,901 | 1/1978 | Seppi et al. | |
| 4,075,484 | 2/1978 | Ebrect et al. | 378/901 |
| 4,082,955 | 4/1978 | Sell | |
| 4,160,909 | 7/1979 | Froggatt | |
| 4,217,641 | 8/1980 | Naparstek | |
| 4,228,515 | 10/1980 | Genna et al. | 364/414 |
| 4,247,774 | 1/1981 | Brooks | |
| 4,264,820 | 4/1981 | Hotta | |
| 4,284,896 | 8/1981 | Stonestrom | |
| 4,309,614 | 1/1982 | Wagner | 378/16 |
| 4,315,156 | 2/1982 | Sell | |
| 4,326,252 | 4/1982 | Kohno et al. | |
| 4,333,145 | 6/1982 | Heuscher et al. | |
| 4,334,153 | 6/1982 | Stehman et al. | 378/113 |
| 4,384,209 | 5/1983 | Wagner et al. | |
| 4,499,493 | 2/1985 | Nishimura | |
| 4,503,461 | 3/1985 | Nishimura | |
| 4,555,760 | 11/1985 | Op De Beek et al. | |
| 4,578,753 | 3/1986 | Crawford et al. | |
| 4,578,803 | 3/1986 | Macovski | |
| 4,580,219 | 4/1986 | Pelc et al. | |
| 4,590,558 | 5/1986 | Glover et al. | |
| 4,639,941 | 1/1987 | Hounsfield | |

FOREIGN PATENT DOCUMENTS

| | | |
|---|---|---|
| 2019688 | 10/1979 | European Pat. Off. |
| 0052394 | 11/1980 | European Pat. Off. |
| 0049484 | 4/1982 | European Pat. Off. |
| 0052269 | 5/1982 | European Pat. Off. |
| 0112487 | 11/1982 | European Pat. Off. |
| 0089096 | 3/1983 | European Pat. Off. |
| 0092787 | 11/1983 | European Pat. Off. |
| 2531477 | 2/1977 | Fed. Rep. of Germany |
| 2636161 | 2/1977 | Fed. Rep. of Germany |
| 2741958 | 4/1978 | Fed. Rep. of Germany |
| 2846702 | 5/1979 | Fed. Rep. of Germany |
| 2846876 | 5/1980 | Fed. Rep. of Germany |
| 3204852 | 8/1982 | Fed. Rep. of Germany |
| 2426343 | 11/1982 | Fed. Rep. of Germany |
| 3401061 | 7/1984 | Fed. Rep. of Germany |
| 2422968 | 11/1979 | France |
| 53-17921 | 2/1978 | Japan |
| 54-25189 | 2/1979 | Japan |
| 55-99241 | 7/1980 | Japan |
| 1601580 | 10/1981 | Japan |
| 2025728 | 1/1980 | United Kingdom |
| 2024559 | 1/1980 | United Kingdom |
| 2049237 | 3/1980 | United Kingdom |
| 2050108 | 5/1980 | United Kingdom |

OTHER PUBLICATIONS

Lehmann et al. "Generalized Image Combinations in Dual KVF Digital Radiography", Med. Phys. vol. 8, Sep./Oct. 1981 pp. 659–667.

Brody et al. "A method for Selective Tissue and Bone Visualization Using Dual Energy Scanned Projection Radiography", 12/15/80 pp. 353–357.

M. Goitein "Three-Dimensional Density Reconstruction From a Series of Two-Dimensional Projections", Nuclear Instruments and Methods (1972) pp. 509–518.

*Primary Examiner*—Carolyn E. Fields
*Assistant Examiner*—Joseph A. Hynds
*Attorney, Agent, or Firm*—Oblon, Fisher, Spivak, McClelland & Maier

[57] ABSTRACT

An X-ray inspection apparatus is provided with main detectors each for detecting the absorption amount of X-ray beams delivered from an X-ray focal point, a reference detector for detecting variations in the size or position of the X-ray focal point, and means for removing errors due to influence of the X-ray focal point variations, based on the detention result of the reference detector.

14 Claims, 10 Drawing Sheets

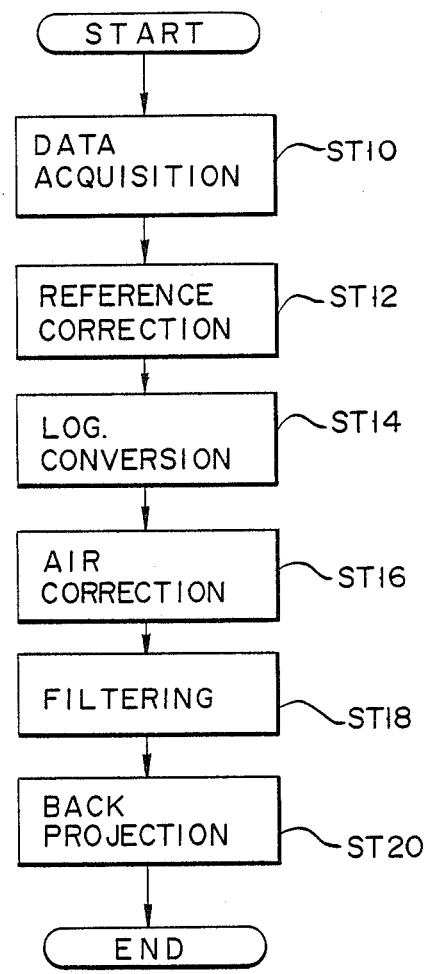

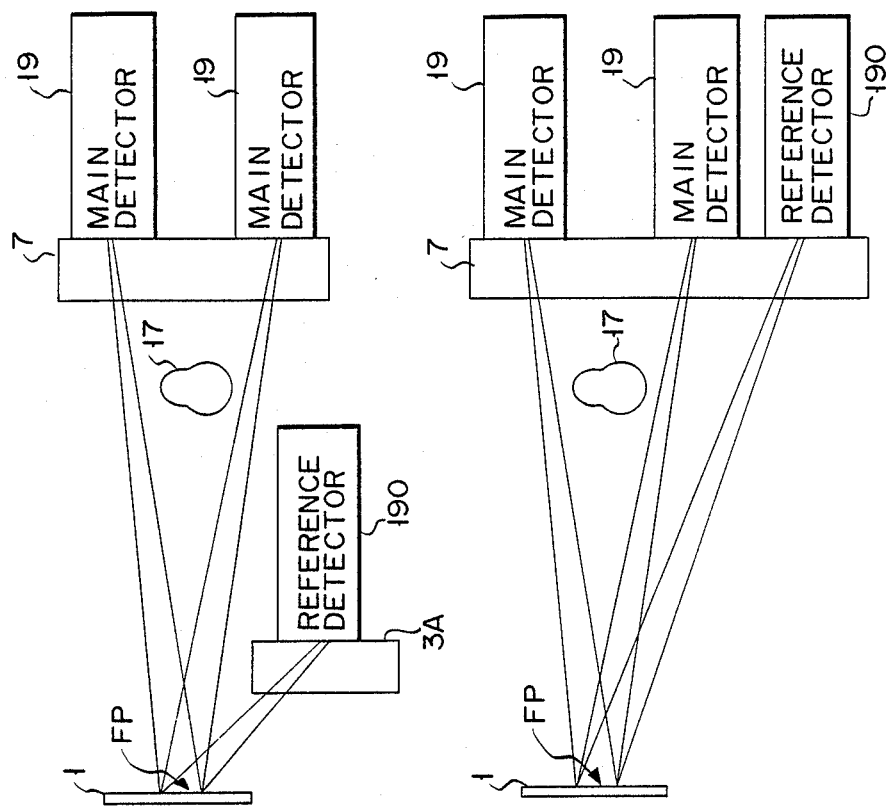

F I G. 5
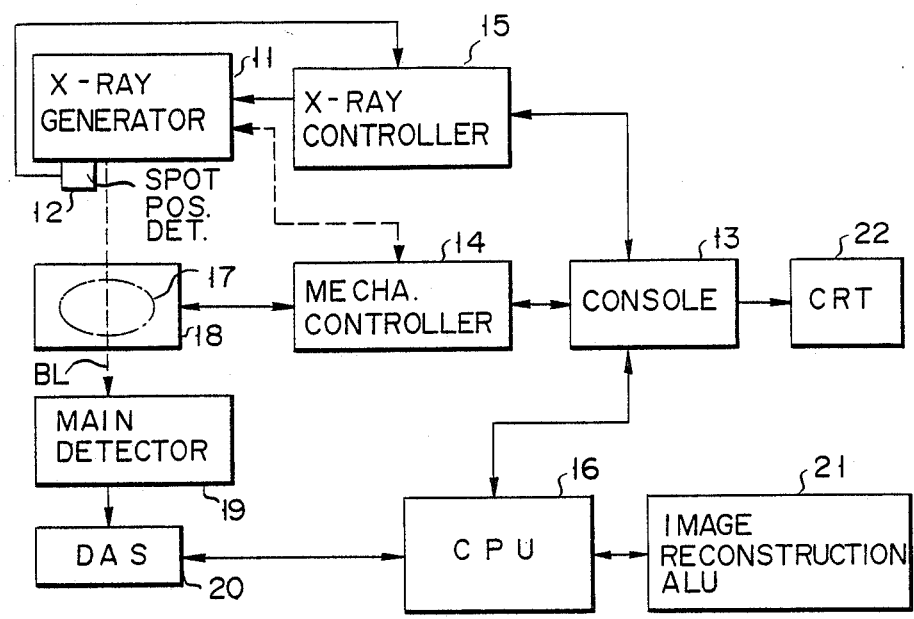
F I G. 6
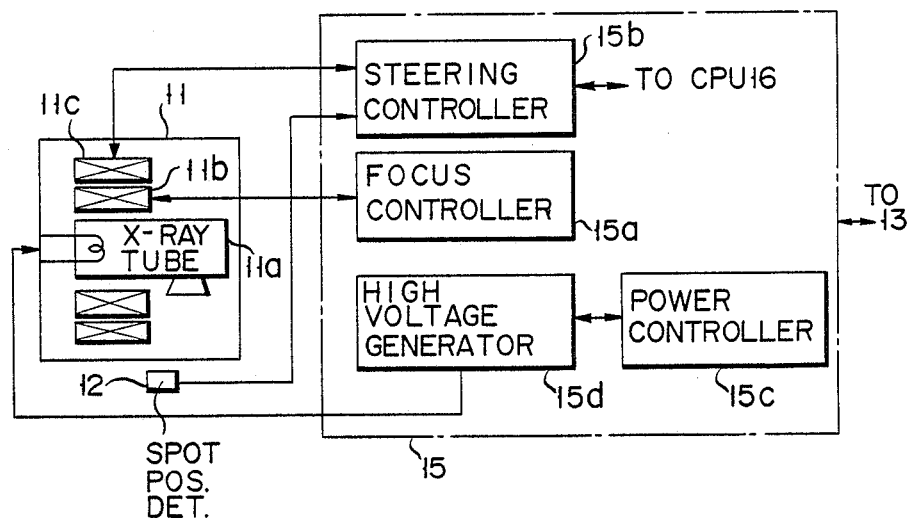

F I G. 14
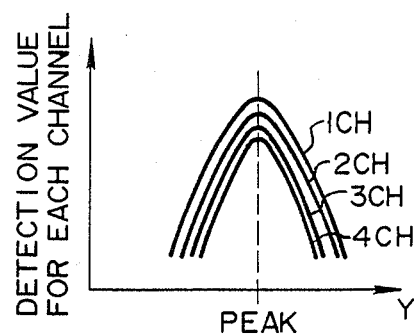
F I G. 15
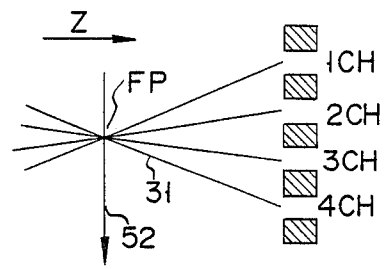
F I G. 16
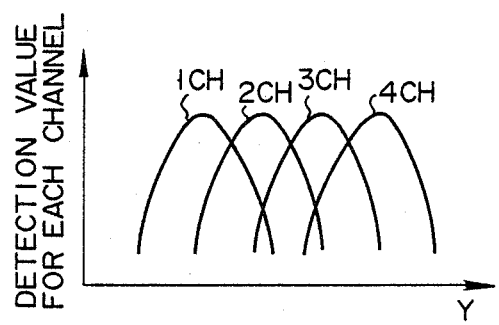
F I G. 17
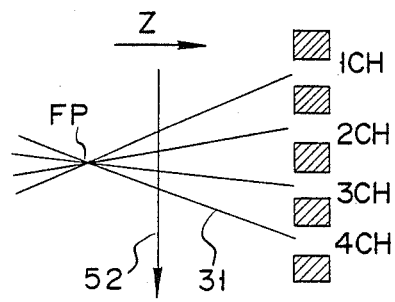

X-RAY INSPECTION APPARATUS

This application is a continuation of application Ser. No. 911,100, filed on Sept. 24, 1986, now abandoned.

BACKGROUND OF THE INVENTION

The present invention relates to an X-ray inspection apparatus (typically an X-ray CT scanner) in which errors due to variations of an X-ray focal point are properly compensated for, thereby improving an accuracy of the result of inspection.

An X-ray source is generally subjected to periodical variations due to ripples of the acceleration voltage of an X-ray tube, which is caused by the existence of a peripheral cap of the X-ray tube filament, and periodical variations due to electrical field variations.

The former ripple variations can be detected as variations in a total X-ray radiation amount per unit time. Further, a recent rectifier circuit for generating the acceleration voltage is highly improved such that the amount of the ripples is at most 1% of the acceleration voltage. Consequently, the ripple variations are no longer serious for a recent technology.

On the other hand, when the X-ray tube filament is powered by an AC current, an electric field for converging hot electrons of the X-ray tube becomes alternative, so that the latter electrical field variations occur. The electrical field variations cause variations in a focal spot size at the X-ray target, thereby producing moires in the reconstructed image of an inspection object. The focal spot size variations do not change the total amount of X-ray radiations per unit time, but they change the X-ray radiation amount per unit area.

An error compensation for X-ray inspection data should be done in consideration not only of the ripple variations, but also of the electrical field variations. However, according to a prior art technology, the electrical field variations can hardly be detected.

Generally, an X-ray inspection apparatus (X-ray CT scanner) is used for a diagnostic purpose and industrial purpose. Recent demand in the industrial purpose is to obtain an extremely high resolution of the order of several microns to several tens microns. Obtaining such a high resolution is new trial for a prior art X-ray CT scanner, and it requires a special microfocus X-ray generator. The focal spot size of 5 $\mu$m to 100 $\mu$m, obtained by such a special microfocus X-ray generator, is roughly 1/100 of the focal spot size of a conventional X-ray generator.

When the X-ray CT scanner operates for a long time to acquire a large amount of inspection data, the position of the microfocal spot is liable to drift with passage of time and/or a change of temperature. If a position drift of the microfocal spot occurs, artifacts appear in the image reconstructed from the acquired inspection data.

Thus, for an extremely high resolution X-ray CT scanner, variations in the microfocal spot size due to electrical field variations, as well as variations in the position of the microfocal spot due to drift, are serious problems.

SUMMARY OF THE INVENTION

It is accordingly an object of the present invention to provide an X-ray inspection apparatus which is free of errors or artifacts due to variations of an X-ray focal point.

To achieve the above object, an X-ray inspection apparatus of the invention is provided with means (190, 12) for detecting variations of an X-ray focal spot, and means (16) for removing influence of the X-ray focal spot variations based on the detection result of the detecting means (190, 12).

BRIEF DESCRIPTION OF THE DRAWINGS

FIG. 2 is a flow chart explaining the operation of CPU 16, DAS 20 and ALU 21 in the embodiment of FIG. 1;

FIG. 3 illustrates a modification of the embodiment of FIG. 1;

FIG. 4 illustrates another modification of the embodiment of FIG. 1;

FIG. 5 shows a configuration of an X-ray CT scanner according to a second embodiment of the present invention;

FIG. 6 shows details of X-ray controller 15 used in the embodiment of FIG. 5;

FIG. 14 illustrates how the detection value of each main detector 19 of respective channels (1ch–4ch) varies with respect to the Y direction, wherein the peak point of each of detection values matches one another;

FIG. 15 shows a relation between focal point FP of X-ray beams 31 and locus 52 of the traverse scan of X-ray beams 31, which relation corresponds to the curves of FIG. 14;

FIG. 16 illustrates how the detection value of each main detector 19 of respective channels (1ch–4ch) varies with respect to the Y direction, wherein the peak point of each of detection values differs from one another;

FIG. 17 shows a relation in which locus 52 is ahead of focal point FP toward detectors, which relation corresponds to the curves of FIG. 16;

DETAILED DESCRIPTION OF THE PREFERRED EMBODIMENTS

Figure 1:
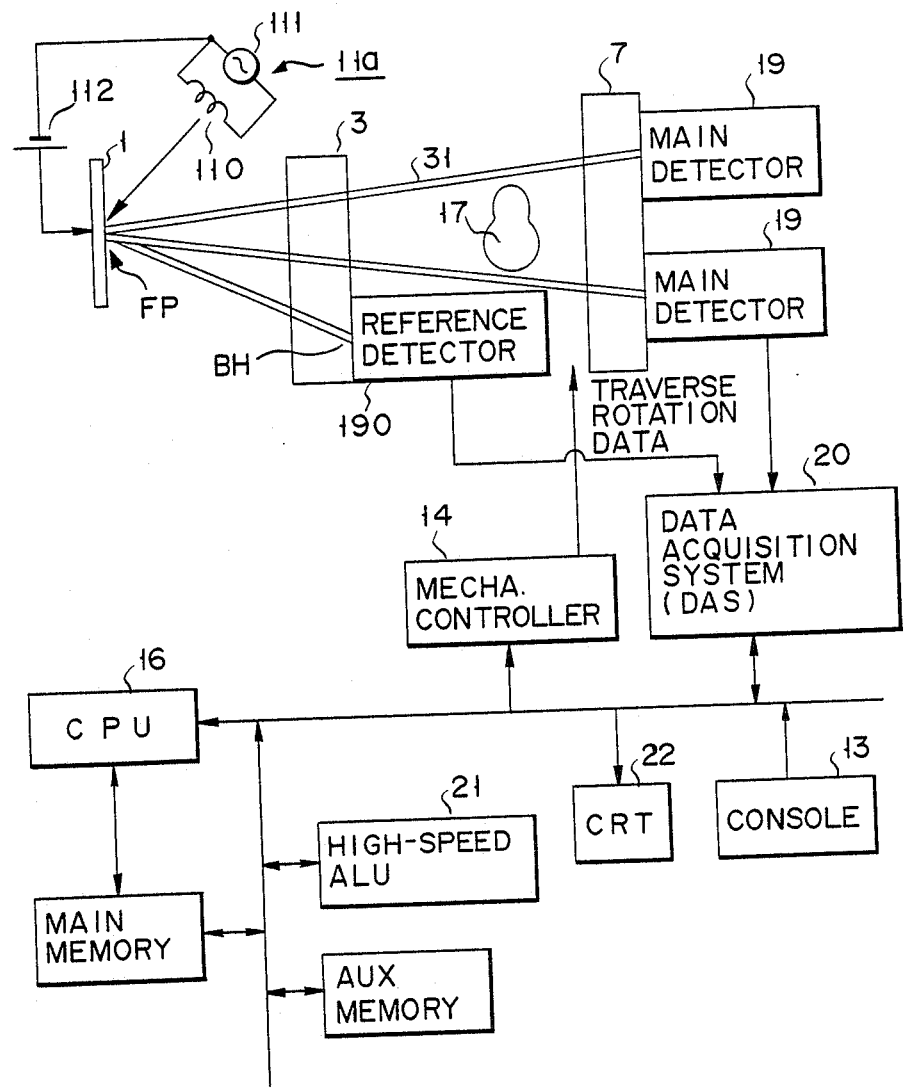
FIG. 1 shows a configuration of an X-ray CT scanner according to a first embodiment of the present invention.

Hereinafter, preferred embodiments of the invention will be described in detail with reference to the accompanying drawings. In the following description, the same or similar elements are denoted by the same or similar reference numerals throughout the drawings, thereby avoiding redundant explanations.

FIG. 1 shows a configuration of a X-ray CT scanner according to a first embodiment of the present invention. Used in this embodiment is a second generation type two channel X-ray CT scanner. Filament 110 of X-ray tube 11a is powered by AC source 111. Hot electrons delivered from filament 110 is accelerated by high voltage 112, and the accelerated electrons run into target 1. X-rays diverged from target 1 are formed into X-ray beams 31 via collimator 3. X-ray beams 31 are projected, via collimator 7, onto main detectors 19 of respective channels. Object 17 to be inspected is disposed between collimators 3 and 7. The magnitude of X-rays beams 31, containing information of the X-ray absorption of object 17, is detected by respective main detectors 19.

Collimator 3 has beam hole BH. Reference detector 190 is mounted on collimator 3, so that detector 190 faces X-ray focal point FP on target 1 via beam hole BH. Thus, focal point FP of X-ray beams 31 for main detectors 19 is the same as that for reference detector 190. Accordingly, variations in the focal spot size at focal point FP, due to said electrical field variations, can be detected by reference detector 190, independently of the detection of main detectors 19. Data of the focal spot size variations, obtained from reference detector 190, is used for correcting electrical field variation errors contained in the X-ray absorption data of object 17.

FIG. 2 is a flow chart explaining the operation of the embodiment in FIG. 1.

The X-ray absorption data of object 17, detected by respective main detectors 19, is input to data acquisition system (DAS) 20. The focal spot size variation data, detected by reference detector 190, is also input to data acquisition system (DAS) 20. DAS 20 acquires data from main and reference detectors 19 and 190 under the control of CPU 16 (ST10). The acquired data is sent from DAS 20 to high-speed arithmetic logic unit (ALU) 21.

When the center of focal point FP for main detectors 19 slightly deviates from that for reference detector 190 because of a mechanical inaccuracy of collimators 3 and 7, phase difference $\phi i$ corresponding to this slight deviation appears between the X-ray absorption data from main detector 19 and the focal spot size variation data from reference detector 190.

Errors due to the above phase difference $\phi i$ are removed by reference correction (ST12) which is performed by CPU 16 based on the acquired data from DAS 20. In the reference correction (ST12), data of X-ray beam 31 from each of detectors 19 is compared with that from detector 190, and variations of X-ray beam data from detectors 19 are corrected by the result of this comparison. Details of the reference correction (ST12) will be described later.

The detected amount of X-ray reduces in accordance with a function of the exponent of an X-ray absorption coefficient. From this, after performing the reference correction, log conversion is effected on the corrected data (ST14).

The log-converted data is subjected to air correction (ST16). By the air correction (ST16), the gain of each of main detectors 19 is adjusted such that the effective gain of one of main detectors 19 matches that of each other main detectors 19.

The air-corrected data is filtered (ST18). A filter with the Raman Chandran function or with the Shep and Logan function may be used in this step ST18.

The filtered data is back-projected in ALU 21 to obtain reconstructed image data (ST20).

Now, descriptions will be given to the reference correction of step ST12.

Periodical variations in the density of X-ray can be represented by a sinusoidal function whose frequency $\omega$ depends on the filament power source frequency of X-ray tube 11a and on the integral of the detected X-ray amount with respect to time.

From the above, if the reference is made on the detected data from reference detector 190, main detection value IMi of ith main detector 19, which is a function of time t, can be expressed as:

$$IMi(t) = [IM] \sin(\omega t + \phi i) + Bi \qquad (1)$$

where i $(= 1, 2, ---, n;$ n is the number of main detectors 19) denotes the numeric order of main detectors 19, [IM] denotes the amplitude of IMi(t), $\omega$ denotes the angular frequency of an AC current for heating the filament of X-ray tube 11a, $\phi i$ denotes phase difference between the data from ith main detector 19 and the data from reference detector 190, and Bi denotes the DC component (bias) of IMi(t).

Reference detection value IR(t) can be expressed as:

$$IR(t) = [IR] \sin \omega t + BR \qquad (2)$$

where [IR] denotes the amplitude of IR(t), and BR denotes the DC component (bias) of IR(t).

Reference correction value IC(t) obtained by a conventional manner is:

$$IC(t) = IMi(t)/IR(t) = Fi(\omega, \mu i(t)) + Bi^* \qquad (3)$$

where Fi($\omega$, $\mu i(t)$) represents a periodic function of angular frequency $\omega$ and Bi* denotes the DC component (bias) of IC(t), in which $\mu i(t)$ denotes the linear integral of an X-ray absorption coefficient with respect to time t.

Equation (3) teaches that reference correction value IC(t) obtained by a conventional manner involves a component of $\omega$, i.e., Fi is subjected to the influence of electrical field variations. However, this influence can be avoided by removing the electrical field variation component of known angular frequency $\omega$ from Fi($\omega$, $\mu i(t)$), provided that the $\omega$ component originally contained in the projection data be remained.

How the electrical field variation component of angular frequency $\omega$ is removed from Fi($\omega$, $\mu i(t)$) will be described below.

In the data acquisition step (SI10), integral $\mu i(t)$ is not zero, and IC(t) is Fi($\omega$, $\mu i(t)$)+Bi*. Then, the Fourier transform F$\mu i$* of IC(t) in the data acquisition is:

$$F\mu i^* = F(Fi(\omega, \mu i(t)) + Bi^*) \qquad (4)$$

Removing the DC component Bi* from Fμi* produces Fμi. This Fμi represents the component of periodical variations and noises of Fμi*.

In the air correction step (SI12), a calibration with no inspection object is performed. In this case, integral μi(t) is zero, and IC(t) is Fi(ω, 0)+Bi*. Then, the Fourier transform Foi* of IC(t) in the air correction is:

$$Foi^* = F(Fi(\omega, 0) + Bi^*) \quad (5)$$

Removing DC component Bi* from Foi* produces Foi. This Foi represents the component of periodical variations and noises of Foi*.

Assume that Fμi* is Fourier-transformed at N points. Then, $$F\mu i^* = F(F\mu i(1), F\mu i(2), \cdots, F\mu i(j), \cdots, F\mu i(N)) \quad (4A)$$

Also assume that Foi* is Fourier-transformed at N points. Then, $$Foi^* = F(Foi(1), Foi(2), \cdots, Foi(j), \cdots, Foi(N)) \quad (5A)$$

Further assume that the ω component of the periodical variations appears at the point(s) of j=k (1≦k≦N) where j=1, 2, ..., N.

When Foi* (Eq. 5A) is subtracted from Fμi* (Eq. 4A), the ω component at the point(s) of j=k is cancelled.

Thus, by subtracting Foi* (Eq. 5) from Fμi* (Eq. 4), the ω component, involved in Fμi*, can be removed. When this ω component-free Fμi* is Fourier inverse-transformed, ω component-free Fμi, representing reference correction value IC(t), is obtained.

According to the above embodiment, an X-ray CT scanner, being free of errors due to electrical field variations or due to variations in the focal spot size of an X-ray, can be obtained.

FIG. 3 illustrates a modification of the embodiment of FIG. 1. In this modification, collimator 3A for reference detector 190 is located out of the path of X-ray beams 31 passing from target 1 to main detectors 19.

FIG. 4 illustrates another modification of the the embodiment of FIG. 1. In this modification, reference detector 190 is mounted on a given side part of collimator 7 on which main detectors 19 are mounted.

FIG. 5 shows a configuration of an X-ray CT scanner according to a second embodiment of this invention. FIG. 6 shows details of X-ray controller 15.

The key feature of the second embodiment resides in the use of spot position detector 12 for X-ray beams. Detector 12 is arranged at X-ray generator 11 and is used for detection variations in the position of an X-ray beam spot. The result of detection of the beam spot variations is supplied to CPU 16. CPU 16 calculates the amount of the beam spot variations. According to this calculation, steering controller 15b (FIG. 6) in X-ray controller 15 controls steering coil 11c such that the position variation amount of the X-ray beam spot is minimized by means of an negative feedback. Details as to such control will be described below.

According to manually input instructions or prescribed sequence control program, console 13 totally governs mechanism controller 14, X-ray controller 15, CPU 16 and display device (CRT) 22. Based on instructions from console 13, mechanism controller 14 drives mechanism 18 on which object 17 to be inspected is mounted. X-ray controller 15 receives, from CPU 16, calculated data of focal spot position variations detected by spot position detector 12, and controls X-ray generator 11 according to the calculated data.

Although CPU 16 depends on the control of console 13, CPU 16 independently has its own program. According to this program, CPU 16 calculates the amount of variations in the focal spot position, based on data from spot position detector 12. (Details of this calculation will be described later.) CPU 16 sends projection data from DAS 20 to image reconstruction ALU 21, so that a CT image of object 17 is reconstructed. The reconstructed CT image is displayed at CRT 22.

As shown in FIG. 6, X-ray generator 11 includes X-ray tube (radiation source) 11a, focus coil 11b and steering coil 11c. X-ray controller 15 includes focus controller 15a, steering controller 15b, power controller 15c and high-voltage generator 15d. A high-potential voltage output from high-voltage generator 15d, which is applied to the filament of X-ray tube 11a, is controlled by power controller 15c. A current flowing through coil 11b is changed by focus controller 15a, and a current flowing through coil 11c is changed by steering controller 15b.

Steering controller 15b sends spot position data, obtained from spot position detector 12, to CPU 16. Then, steering controller 15b receives position calculation data from CPU 16, and controls steering coils 11c based on the position calculation data. The electron beam generated from tube 11a is thus controlled by controllers 15a and 15b.

Figure 7:
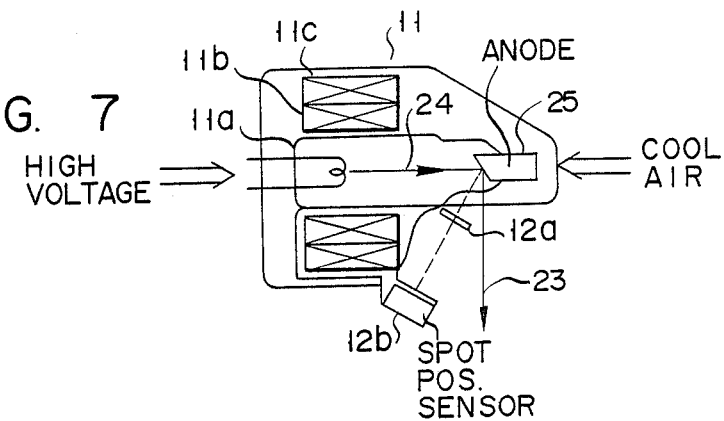
FIG. 7 shows details of X-ray generator 11 used in the embodiment of FIG. 5.
Figure 8:
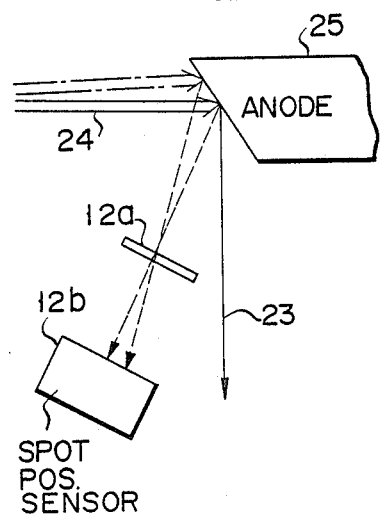
FIG. 8 illustrates the path of X-ray beam 23 and electron beam 24 near anode 25 of the X-ray tube and near spot position detector 12b.

FIG. 7 shows a configuration of X-ray generator 11. FIG. 8 illustrates the path of X-ray beams 23 and electron beams 24 near anode 25 of X-ray tube 11a.

Spot position detector 12 is formed of pin hole plate 12a and spot position sensor 12b. As shown in FIG. 7 and 8, the path of the input beam of sensor 12b deviates from the path of X-ray beams 23. X-ray beams 23 are generated from anode 25 of X-ray tube 11a, upon excitations of electron beams 24 from the filament of X-ray tube 11a. The path of the input beam of sensor 12b is defined by pin hole plate 12a. The pin hole diameter of plate 12a is selected to be substantially equal to the diameter of an X-ray focal spot (FP). Plate 12a is made of a heavy metal.

Figure 9:
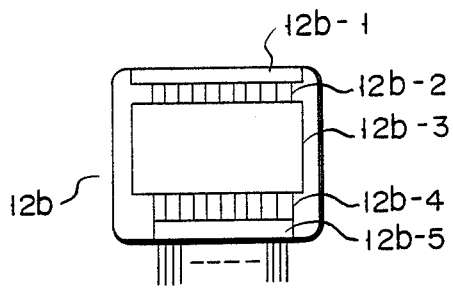
FIG. 9 shows the front view of spot position sensor 12b which is a part of spot position detector 12 used in the embodiment of FIG. 5.

FIG. 9 shows the front view of spot position sensor 12b which is a part of spot position detector 12. Sensor 12b is formed of fluophor 12b-1, light guide fibers 12b-2, microchannel plate 12b-3, light guide fibers 12b-4 and position sensor element 12b-5. Fluophor 12b-1 is light-excited by the input X-ray. Light outputs from fluophor 12b-1 are sent via fibers 12b-2 to microchannel plate 12b-3, in which the light outputs are channel-divided. The channel-divided light outputs from plate 12b-3 are sent via fibers 12b-4 to position sensor element 12b-5. The channel-divided light outputs are converted into electric signals (position data) by element 12b-5.

Figure 10:
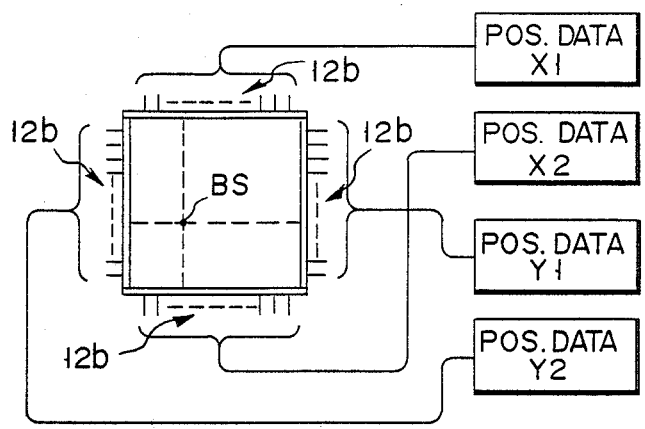
FIG. 10 illustrates how the position of beam spot BS is detected by spot position sensors 12b.

FIG. 10 illustrates how the position of beam spot BS on the sensor plane of detector 12 is detected by spot position sensors 12b.

Four sets of spot position sensors 12b are arranged at respective four sides of the square or rectangular X-ray sensor plane (X-Y plane) of spot position detector 12. (This X-Y plane corresponds to the target of X-ray tube 11a.) The X-axis position of beam spot BS on the X-ray sensor plane is detected by upper side and lower side sensors 12b, and the Y-axis position thereof is detected by right side and left side sensors 12b. X-axis position data X1 is obtain by upper side sensor 12b. X-axis position data X2 is obtain by lower side sensor 12b. Y-axis position data Y1 is obtain by right side sensor 12b. Y-axis position data Y2 is obtain by left side sensor 12b.

Figure 11:
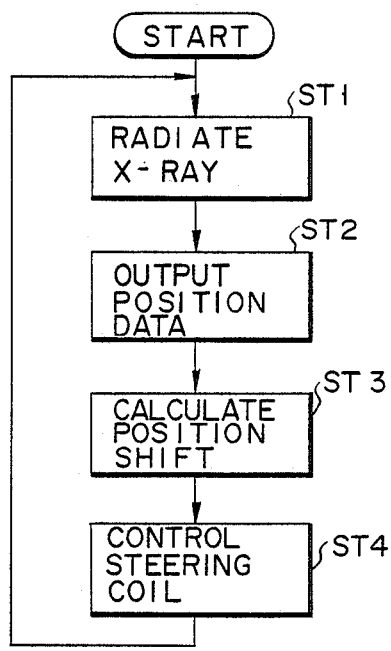
FIG. 11 is a flow chart explaining the operation of circuit elements 13–20 in the embodiment of FIG. 5.

FIG. 11 is a flow chart explaining the position adjusting routine of beam spot BS. This routine starts according to a manual instruction via console 13, or according to a given sequence program, before the start of data acquisition or during the operation of data acquisition.

After starting the position adjusting routine, X-ray beams 23 are radiated from anode 25 of X-ray tube 11a (ST1 in FIG. 11). Along with this X-ray radiation, each of spot position sensors 12b senses, via pin hole plate 12a, a part of beams 23 to generate position data X1, X2, Y1 and Y2 (ST2 in FIG. 11). These position data X1, X2, Y1 and Y2 are collected by steering controller 15b, and the collected position data are sent to CPU 16 via console 13.

In CPU 16, the following calculations are performed according to position data X1, X2, Y1 and Y2:

$$X = (X1 - X2)/(X1 + X2) \quad (6)$$

$$Y = (Y1 - Y2)/(Y1 + Y2) \quad (7)$$

The coordinates of X and Y, represented by equations (6) and (7), defines the location of beam spot BS in the X-Y plane of spot position detector 12.

Assume that coordinates of a predetermined reference position in the X-Y plane of spot position detector 12 are denoted by Xo and Yo. Then, the amount of a position shift of beam spot BS from the reference position can be calculated from the following equations:

$$\Delta X = Xo - X \quad (8)$$

$$\Delta Y = Yo - Y \quad (9)$$

The position shift of beam spot BS with respect to the normal direction (Z direction) of the X-Y plane can be determined as follows.

Assume that, when no position shift of Z direction appears, the area of beam spot BS formed on the X-Y plane of spot position detector 12 is denoted by So. Assume that, if a certain position shift of Z direction appears, the area of beam spot BS formed on the X-Y plane of spot position detector 12 is denoted by S. Further assume that, after completing the control for minimizing the value of $\Delta X$ and $\Delta Y$ of equations (8) and (9), $|X1 - X2|$ is substantially equal to $|Y1 - Y2|$.

Under the above assumptions, the value of area S can be approximately represented by:

$$S = (\pi/4)|(X1 - X2)| \cdot |(Y1 - Y2)| \quad (10)$$

Then, the amount of a position shift of beam spot BS along Z direction can be calculated from the following equation:

$$\Delta S = |So - S| \quad (11)$$

Position shift data ($\Delta X$, $\Delta Y$, $\Delta S$) of beam spot BS with respect to X, Y and Z directions are thus obtained in CPU 16, based on equations (8), (9) and (11) (ST3 in FIG. 11).

Calculated position shift data ($\Delta X$, $\Delta Y$, $\Delta S$) of beam spot BS are then sent from CPU 16 to steering controller 15b. Then, the current of steering coil 11c is controlled according to the calculated position shift data ($\Delta X$, $\Delta Y$, $\Delta S$), so that the amount of each of $\Delta X$, $\Delta Y$ and $\Delta S$ reduces (ST4 in FIG. 11).

The above steps ST1 to ST4 are repeated to minimize the amount of each of $\Delta X$, $\Delta Y$ and $\Delta S$. This operation is of a digital negative feedback control whose control targets are predetermined by Xo, Yo and So. According to this feedback operation, variations in the position of a microfocal spot, due to drift with passage of time and/or a change of temperature, can be practically removed. This feedback operation may not be always performed, but performed as the case may require. Further, since the mechanical part of this feedback operation is constituted by a conventional steering coil, the total configuration can be made simple.

Figure 12:
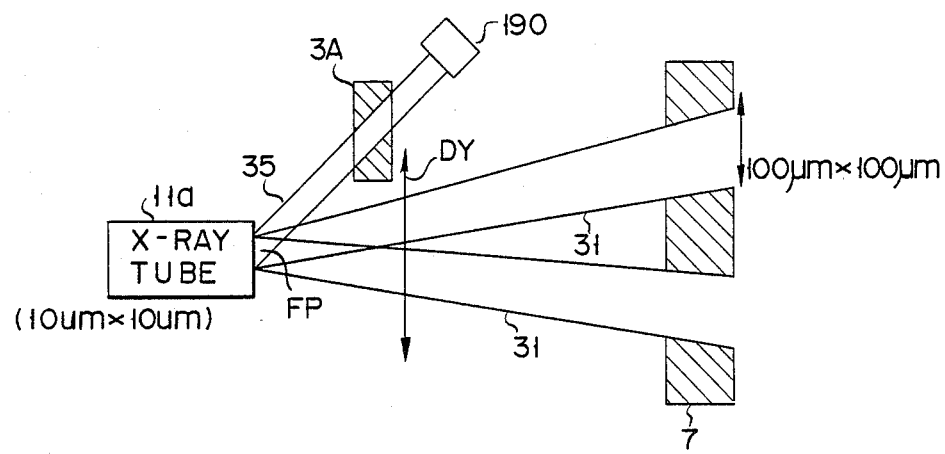
FIG. 12 illustrates how the embodiment of FIG. 3 il applied to the embodiment of FIG. 5.
Figure 13:
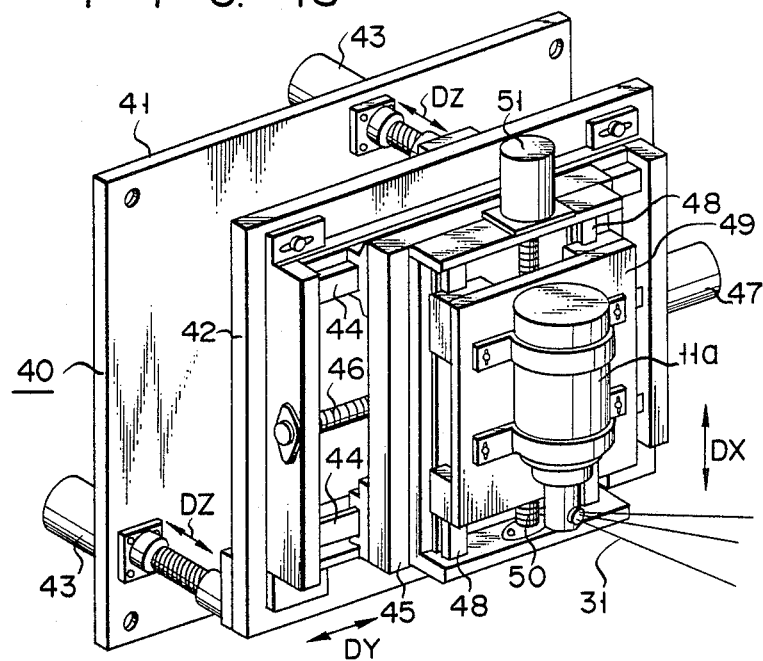
FIG. 13 is a perspective view of a spot position adjusting mechanism on which X-ray tube 11a is movably mounted.

FIG. 12 illustrates how the embodiment of FIG. 3 is applied to the embodiment of FIG. 5. FIG. 13 is a perspective view of a spot position adjusting mechanism on which X-ray tube 11a is movably mounted.

In the embodiment of FIG. 12, aforementioned electrical field variations are detected by the combination of collimator 3A and reference detector 190, and position variations of a focal spot (FP) are cancelled out by the mechanical operation of the spot position adjusting mechanism of FIG. 13.

As shown in FIG. 12, the size of X-ray beams 31 at the side of main detectors (19) is limited by the aperture size of collimator 7, and it may have 100 $\mu$m × 100 $\mu$m. On the other hand, the size of microfocal point FP on the target of X-ray tube 11a may have 10 $\mu$m × 10 $\mu$m. Although not shown in FIG. 12, X-ray tube 11a may be provided with pin hole plate 12a and spot position sensor 12b, as shown in FIG. 7.

The normal of the hole (aperture) of each of collimators 3A and 7 is directed to the target of X-ray tube 11a. When the position of focal point FP on the target is shifted, the amount of X-ray, detected by each of reference detector 190 and main detectors 19 (not shown in FIG. 12, but shown in FIG. 3), varies similarly. Thus, the variations in the amount of X-ray detected by detectors 19 can be known from the variations in the amount of X-ray detected by detector 190. Based on the output from detector 190, influence of said electrical field variations, involved in the output from detectors 19, can be eliminated, as in the case of FIG. 1. (Arrow DY in FIG. 12 indicates the traverse direction when a second generation CT scanner is used.)

Incidentally, if the filament of X-ray tube 11a is powered by DC, since no electrical field variations occur, the combination of collimator 3A and reference detector 190 may be omitted.

When the filament of X-ray tube 11a is powered by AC and electrical field variations occur, periodical variations of detected X-ray, which are independ of the variations in the position of focal point FP, will appear. However, the total amount of X-ray radiations per unit time is free of the periodical variations due to the electrical field variations, as mentioned in the background of the invention. Consequently, CPU 16 in FIG. 1 or 5 responds to the total amount of X-ray radiations for each one traverse scan of the second generation CT scanner. Then, CPU 16 can detect the variations in the position of focal point FP without influence of the electrical field variations.

To be concrete, if the value of the total amount of X-ray radiations for each one traverse scan becomes less than the 90% of the total amount value that obtained with no position variation of focal point FP, CPU 16 detects an actual position variation of focal point FP.

Then, CPU 16 starts the control for removing the actual position variation of focal point FP.

The spot position adjusting mechanism for X-ray tube 11a is shown in FIG. 13. X-ray tube 11a is mounted on movable table mechanism 40. Table mechanism 40 is formed of base 41 and first table 42 which is parallel arranged to base 41. Table 42 is supported, at three point, by three Z-axis adjusting actuators (electrically operating cylinder or the like) 43. The actuating direction of each of actuators 43 is dented by DZ in FIG. 13. The inclination of table 42 with respect to base 41 can be optionally changed by each independent actuation of actuators 43.

Table 42 is provided with two parallel rails 44 on which second table 45 is movably supported. Table 42 is also provided with Y-axis adjusting actuator 47. Actuator 47 rotates screw 46, so that table 45 moves in Y-axis direction DY along rails 44.

Table 45 is provided with two parallel rails 48 on which third table 49 is movably supported. Table 45 is also provided with X-axis adjusting actuator 51. Actuator 51 rotates screw 50, so that table 49 moves in X-axis direction DX along rails 48.

X-ray tube 11a for generating X-ray beams 31 is mounted on above table 49. Thus, X-ray tube 11a can move along any of X, Y and Z directions by the actuation of actuators 43, 47 and 51.

Assume that the main detectors (19) used in the embodiment of FIG. 5 are formed of four channel detectors (1CH—4CH), and this embodiment is provided with the spot position adjusting mechanism shown in FIG. 13.

FIG. 14 illustrates how the detection value of each main detector 19 of respective channels (1ch-4ch) varies with respect to the Y (traverse) direction. The curves of FIG. 14 can be obtained when the radiating point of X-ray beams 31 shifts along the traverse direction for a certain width which is 3 or 4 times larger than the focal spot size (e.g., 10 μm) of beams 31. The locus of this traverse X-ray beam shift is denoted by 52 in FIG. 14. FIG. 14 shows a case in which no position variations of focal point FP along Z direction appear, as shown in FIG. 15, and the peak point of each of X-ray detection values matches one another.

FIG. 16 also illustrates how the detection value of each main detector 19 of respective channels (1ch-4ch) varies with respect to the Y (traverse) direction. FIG. 16 shows a case in which position variations of focal point FP along Z direction appear, as shown in FIG. 17, and the peak point of each of X-ray detection values differs from one another. FIG. 17 shows a relation in which locus 52 is ahead of focal point FP toward detectors (19).

Figure 18:
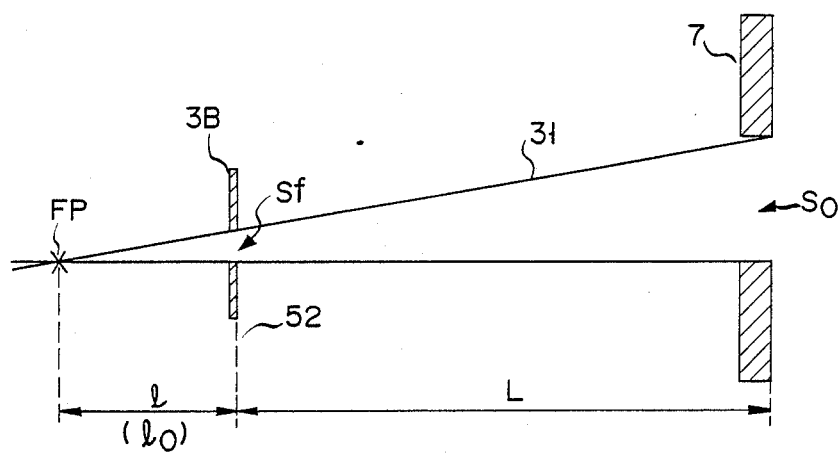
FIG. 18 explains how the distance (l) between focal point FP and locus 52 is calculated.

FIG. 18 explains how the distance (l) between focal point FP and locus 52 is calculated.

Assume that reference plate 3B is located on locus 52, that the distance between focal point FP and the slit (aperture) of reference plate 3B is lo when focal point FP matches locus 52, that the distance between focal point FP and the slit of reference plate 3B is l when focal point FP deviates from locus 52, that the distance between the slit of reference plate 3B and the aperture of collimator 7 is L, that the area of the slit of plate 3B is Sf, that the area of the aperture of collimator 7 is So when focal point FP matches locus 52, that the area of the aperture of collimator 7 is S when focal point FP deviates from locus 52, and that the solid angle of the slit of plate with respect to focal point FP is ψ.

Then, areas Sf and So are:

$$Sf = (4\pi/\psi) \cdot lo^2 \tag{12}$$

$$So = (4\pi/\psi) \cdot (lo + L)^2 \tag{13}$$

When term ψ of So is erased by term ψ of Sf, then, So is:

$$So = Sf \cdot \{(lo + L)/lo\}^2 \tag{14}$$

Meanwhile area S can be represented by:

$$S = Sf \cdot \{(l + L)/l\}^2 = Sf \cdot (1 + L/l)^2 \tag{15}$$

From equations (14) and (15), difference ΔS between S and So is:

$$\Delta S = S - So = Sf \cdot (1 + L/l)^2 - So \tag{16}$$

By modifying equation (16) with respect to distance l, the following relation is obtained:

$$l = L/[\{(So + \Delta S)/Sf\}^{\frac{1}{2}} - 1] \tag{17}$$

Then, difference Δl between l and lo is:

$$\Delta l = l - lo \tag{18}$$

Actuators 43 of FIG. 13 are controlled by CPU 16 via mechanical controller 14, so that the value of Δl is minimized.

Figure 19:
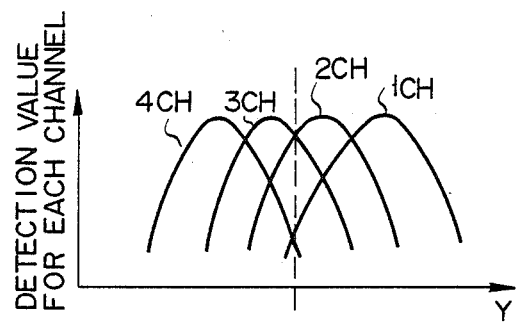
FIG. 19 illustrates how the detection value of each main detector 19 of respective channels (1ch–4ch) varies with respect to the Y direction, wherein the peak point of each detection values differs from one another.
Figure 20:
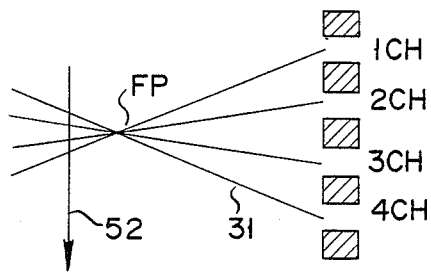
FIG. 20 shows a relation in which locus 52 is behind from focal point FP, which relation corresponds to the curves of FIG. 19.

FIG. 19 illustrates how the detection value of each main detector 19 of respective channels (1ch-4ch) varies with respect to the Y (traverse) direction. FIG. 19 shows a case in which position variations of focal point FP along Z direction appear, as shown in FIG. 20, and the peak point of each of X-ray detection values differs from one another. FIG. 20 shows a relation in which locus 52 is behind from focal point FP.

The distance (l) between focal point FP and locus 52 can be calculated from equation (17), and actuators 43 are controlled, via mechanical controller 14, by CPU 16 so that the value of Δl of equation (18) is minimized.

The above-mentioned Z-axis control, using actuators 43, in case of FIG. 20, is the same as that in case of FIG. 17, except for the sign of difference Δl.

Incidentally, Y-axis control, using actuator 47, is performed, via mechanism controller 14, by CPU 16, such that ΔY of equation (9) is minimized. X-axis control, using actuator 51, is performed, via mechanism controller 14, by CPU 16, such that ΔX of equation (8) is minimized.

Figure 21:
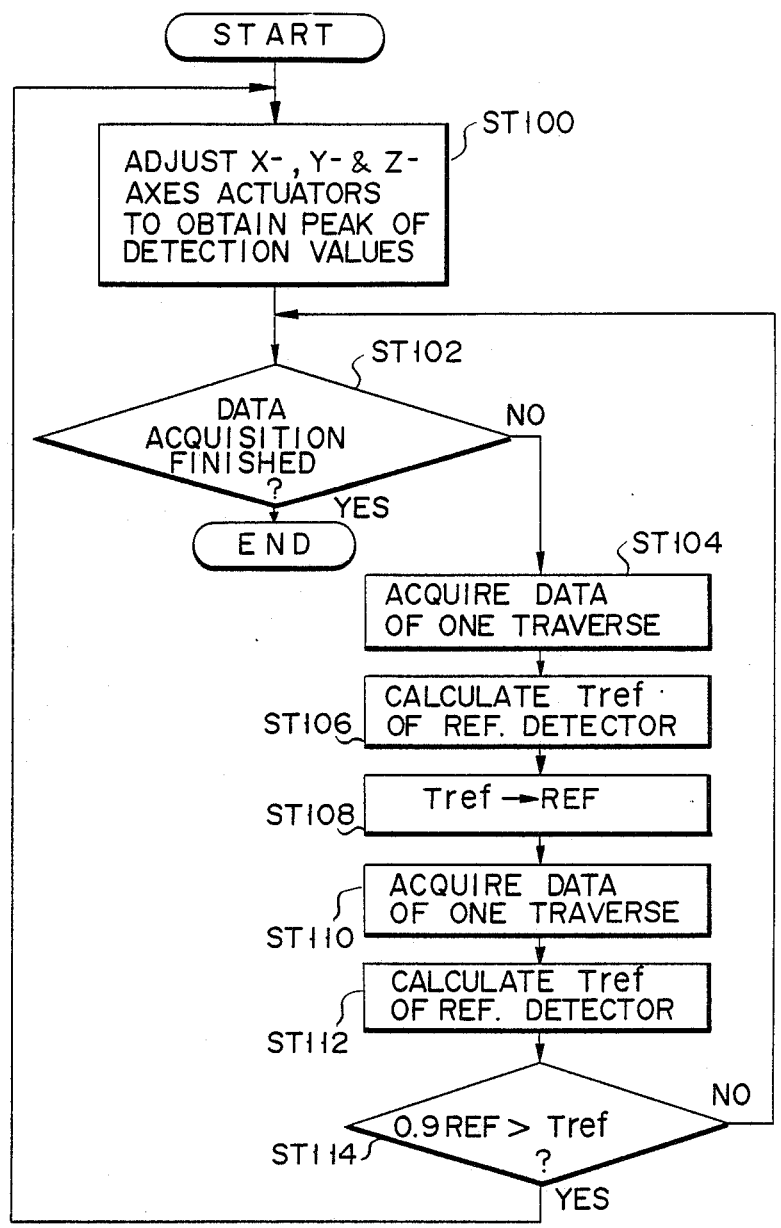
FIG. 21 is a flow chart explaining how DAS 20 in the embodiment of FIG. 5 performs the data acquisition of X-ray projection data.

FIG. 21 is a flow chart explaining how DAS 20 in the embodiment of FIG. 5 performs the data acquisition of X-ray projection data.

Before performing the acquisition of X-ray radiation data, X-, Y- and Z-axes actuators 51, 47 and 43 are adjusted by mechanism controller 14, so that the peak value of each channel is obtained (ST100). (This adjustment can be performed during the X-ray data acquisition process, as the case may be.) Then, if the data acquisition is not finished (NO in ST102), radiation data from reference detector 190 (FIG. 12) is acquired for one traverse direction DY (ST104). The total sum Tref of the acquired data from reference detector 190 is calculated by CPU 16 (ST106). The calculated Tref is stored, as reference REF, in a memory (not shown in FIG. 5, but shown in FIG. 1) of CPU 16 (ST108).

In the subsequent one traverse scanning, radiation data from reference detector 190 is again acquired (ST110), and the total sum Tref of the next acquired data is calculated by CPU 16 (ST112). The second calculated Tref is compared with the 90% of the stored reference REF (ST114).

If 0.9 REF>Tref (YES in ST114), substantial variations appear in the position of focal spot FP, and the flow returns to ST100. Then, the position variations of focal spot FP is reduced by the adjustment of ST100. The chain of this flow is repeated until 0.9 REF≦Tref is obtained. Namely, if the value of Tref for each one traverse scan becomes less than the 90% of REF, CPU 16 detects actual position variations of focal point FP. Then, CPU 16 starts the control for removing the actual position variation of focal point FP, as mentioned before.

When 0.9 REF≦Tref (NO in ST114) is obtained, there are not substantial variations in the position of focal spot FP, and the flow returns to ST102. The chain of this flow is repeated until the data acquisition is finished (YES in ST102).

As will be seen from the foregoing description, when the present invention is applied to an extremely high resolution X-ray CT scanner, influence of variations in the microfocal spot size due to electrical field variations, as well as influence of variations in the position of the microfocal spot due to drift, can be removed.

While the invention has been described in connection with what is presently considered to be the most practical and preferred embodiment, it is understood that the invention is not to be limited to the disclosed embodiment but, on the contrary, is intended to cover various modifications and equivalent arrangements included within the spirit and scope of the appended claims which scope is to be accorded the broadest interpretation so as to encompass all such modifications and equivalent structures. For instance, the present invention can be applied not only to a second generation CT scanner, but also to a first, third or fourth generation CT scanner. Further, the occurrence of variations of focal spot FP can be simply detected by a manner in which the detected amount of X-ray falls below a predetermined value, if the filament of X-ray tube 11a is powered by DC. In addition, so long as necessary peak detection values for each channel (cf. FIG. 14) are obtained, only one or two of X-, Y- and Z-axes adjustments, using actuators 51, 47 and 43 in FIG. 13, may be done.

What is claimed is:

1. An X-ray inspection apparatus comprising:
   radiation means, having a focal point, for radiating X-ray beams;
   main X-ray detector means, responsive to the X-ray beams passing through an object to be inspected, for detecting a radiation amount of the X-ray beams to provide projection data of said object; and
   variation detector means, facing said focal point, for detecting variations in size of said focal point, and removing errors, contained in said projection data and caused by the focal point size variations, based on the result of the detection of said focal point size variations.

2. An apparatus according to claim 1, wherein said main detector means includes:
   a main collimator having an aperture which is directed to the focal point of said radiation means: and
   said main X-ray detector means arranged at the position of the aperture of said main collimator to detect the radiation amount of the X-ray beams and to provide the projection data of said object;
   and wherein said variation detector means includes:
   a reference collimator having an aperture which is directed to the focal point of said radiation means; and
   a reference X-ray detector arranged at the position of the aperture of said reference collimator to detect variations in the size of the focal point of said radiation means and to provide reference data which is used to remove said errors.

3. An apparatus according to claim 1, wherein said main detector means includes:
   a collimator having main and reference apertures both of which are directed to the focal point of said radiation means; and
   a main X-ray detector arranged at the position of the main aperture of said collimator to detect the radiation amount of the X-ray beams and to provide the projection data of said object,
   and wherein said variation detector means includes:
   a reference X-ray detector arranged at the position of the reference aperture of said collimator to detect variations in the size of the focal point of said radiation means and to provide reference data which is used to remove said errors.

4. An apparatus according to claim 1, wherein said radiation means includes:
   an X-ray tube, whose anode generates X-rays, for providing said X-ray beams,
   spot position detector means, responsive to the X-ray beams from said anode, for detecting the position of a beam spot of said X-ray beams to provide beam spot position data; and
   spot position control means, coupled to said X-ray tube and said spot position detector means, for controlling said X-ray tube according to said beam spot position data, such that the position of said beam spot, detected by said spot position detector means, approaches to a predetermined reference position.

5. An apparatus according to claim 4, wherein said main detector means includes:
   a main collimator having an aperture which is directed to the focal point at the anode of said X-ray tube; and
   a main X-ray detector arranged at the position of the aperture of said main collimator to detect the radiation amount of the X-ray beams and to provide the projection data of said object,
   and wherein said variation detector means includes:
   a reference collimator having an aperture which is directed to the focal point of said X-ray tube; and
   a reference X-ray detector arranged at the position of the aperture of said reference collimator to detect variations in the size of said focal point and to provide reference data which is used to remove said errors.

6. An apparatus according to claim 5, wherein said radiation means is provided with:
   means for changing a relative distance between the focal point of said X-ray tube and said main X-ray detector means, and wherein said spot position control means includes:

means, coupled to said main X-ray detector means, for controlling said means for changing according to a detection value of the radiation absorption amount of said X-ray beams, such that the position of said focal point approaches to a predetermined place.

7. An apparatus according to claim 4, wherein said radiation means is provided with:

means for changing the relative distance between the focal point of said X-ray tube and said main X-ray detector means, and wherein said spot position control means includes:

means, coupled to said main X-ray detector means, for controlling said means for changing according to the detected radiation amount of said X-ray beams, such that the position of said focal point approaches to a predetermined place.

8. An apparatus according to claim 2, wherein said variation detector means includes:

calculation means for Fourier-transforming a first reference correction value, which is obtained by dividing detection data from said main X-ray detector means by detection data from said reference X-ray detector when said object is under inspection, to provide first Fourier-transformed data; for Fourier-transforming a second reference correction value, which is obtained by dividing detection data from said main X-ray detector means by detection data from said reference X-ray detector when no object is under inspection, to provide second Fourier-transformed data; for subtracting said second Fourier-transformed data from said first Fourier-transformed data to provide Fourier-transformed difference data, so that a component, which corresponds to variations in the size of said focal point and is involved in said first Fourier-transformed data, is substantially eliminated from said Fourier-transformed difference data; and for Fourier-inverse-transforming said Fourier-transformed difference data to provide projection data which is free of said errors due to variations in the size of said focal point.

9. An apparatus according to claim 3, wherein said variation detector means includes:

calculation means for Fourier-transforming a first reference correction value, which is obtained by dividing detection data from said main X-ray detector by detection data from said reference X-ray detector when said object is under inspection, to provide first Fourier-transformed data; for Fourier-transforming a second reference correction value, which is obtained by dividing detection data from said main X-ray detector by detection data from said reference X-ray detector when no object is under inspection, to provide second Fourier-transformed data; for subtracting said second Fourier-transformed data from said first Fourier-transformed data to provide Fourier-transformed difference data, so that a component, which corresponds to variations in the size of said focal point and is involved in said first Fourier-transformed data, is substantially eliminated from said Fourier-transformed difference data; and for Fourier-inverse transforming said Fourier-transformed difference data to provide projection data which is free of said errors due to variations in the size of said focal point.

10. An apparatus according to claim 4, wherein said spot position detector means includes:

means for starting approaching of the beam spot position to said predetermined reference positon, when a total radiation amount of the X-ray beams, detected by said variation detector means for a given period of time, is less than a prescribed value.

11. An X-ray CT scanner comprising:

X-ray generator means for generating X-ray beams for a given focal point;

main X-ray detector means, facing said given focal point, for detecting an amount of the X-ray beams passing through an object to provide projection data of an object to be inspected; and reference detector means, facing said focal point, for detecting variations in size of said focal point, and removing errors, contained in said projection data and caused by the focal point size variations, based on the result of the detection of said focal point size variations.

12. An X-ray CT scanner according to claim 11, comprising:

focal point detector means, facing said given focal point and being located at a position which deviates from an X-ray beam path defined between said given focal point and said main detector means, for detecting variations in the position of said focal point; and position control means, coupled to said X-ray generator means and said focal point detector means, for controlling the position of said given focal point, such that errors, contained in said projection data and caused by the focal point position variations, are removed based on the detected focal point position variations.

13. An X-ray inspection apparatus comprising:

radiation means, having a focal point, for radiating X-ray beams;

main X-ray detector means, responsive to the X-ray beams passing through an object to be inspected, for detecting a radiation amount of the X-ray beams to provide projection data of said object; and variation detector means, facing said focal point, for detecting variations of said focal point, and removing errors, contained in said projection data and caused by the focal point variations, based on the result of the detection of said focal point variations;

wherein said main X-ray detector means includes:

a main collimator having an aperture which is directed to the focal point of said radiation means; and a main X-ray detector arranged at the position of the aperture of said main collimator to detect the radiation amount of the X-ray beams and to provide the projection data of said object, and wherein said variation detector means includes:

a reference collimator having an aperture which is directed to the focal point of said radiation means; and a reference X-ray detector arranged at the position of the aperture of said reference collimator to detect variations of the focal point of said radiation means and to provide reference data which is used to remove said errors;

wherein said variation detector means includes:

calculation means for Fourier-transforming a first reference correction value, which is obtained by dividing detection data from said main X-ray detector by detection data from said reference X-ray detector when said object is under inspection, to provide first Fourier-transformed data; for Fourier-transforming a second reference correction value, which is obtained by dividing detection data from said main X-ray detector by detection data from said reference X-ray detector when no object is under inspection, to provide second Fourier-transformed data; for subtracting said second Fourier-transformed data from said first Fourier-transformed data to provide Fourier-transformed difference data, so that a component, which corresponds to variations of said focal point and is involved in said first Fourier-transformed data, is substantially eliminated from said Fourier-transformed difference data; and for Fourier-inverse-transforming said Fourier-transformed difference data to provide projection data which is free of said errors due to variations of said focal point.

14. An X-ray inspection apparatus comprising:

radiation means, having a focal point, for radiating X-ray beams;

main X-ray detector means, responsive to the X-ray beams passing through an object to be inspected, for detecting a radiation amount of the X-ray beams to provide projection data of said object; and variation detector means, facing said focal point, for detecting variations of said focal point, and removing errors, contained in said projection data and caused by the focal point variations, based on the result of the detection of said focal point variations;

wherein said main X-ray detector means includes:

a collimator having main and reference apertures both of which are directed to the focal point of said radiation means; and a main X-ray detector arranged at the position of the main aperture of said collimator to detect the radiation amount of the X-ray beams and to provide the projection data of said object, and wherein said variation detector means includes:

a reference X-ray detector arranged at the position of the reference aperture of said collimator to detect variations of the focal point of said radiation means and to provide reference data which is used to remove said errors;

wherein said variation detector means includes:

calculation means for Fourier-transforming a first reference correction value, which is obtained by dividing detection data from said main X-ray detector by detection data from said reference X-ray detector when said object is under inspection, to provide first Fourier-transformed data; for Fourier-transforming a second reference correction value, which is obtained by dividing detection data from said main X-ray detector by detection data from said reference X-ray detector when no object is under inspection, to provide second Fourier-transformed data; for subtracting said second Fourier-transformed data from said first Fourier-transformed data to provide Fourier-transformed difference data, so that a component, which corresponds to variations of said focal point and is involved in said first Fourier-transformed data, is substantially eliminated from said Fourier-transformed difference data; and for Fourier-inverse-transforming said Fourier-transformed difference data to provide projection data which is free of said errors due to variations of said focal point.

* * * * *